US006364873B1

(12) United States Patent
McMillen et al.

(10) Patent No.: US 6,364,873 B1
(45) Date of Patent: Apr. 2, 2002

(54) OPHTHALMOLOGICAL SURGERY TECHNIQUE WITH ACTIVE PATIENT DATA CARD

(75) Inventors: Alan R. McMillen, Woodside; Terrance N. Clapham, Saratoga; Charles R. Munnerlyn, Sunnyvale, all of CA (US)

(73) Assignee: Visx Incorporated, Santa Clara, CA (US)

( * ) Notice: Subject to any disclaimer, the term of this patent is extended or adjusted under 35 U.S.C. 154(b) by 0 days.

(21) Appl. No.: 08/904,199

(22) Filed: Jul. 31, 1997

Related U.S. Application Data

(63) Continuation of application No. 07/666,840, filed on Mar. 8, 1991.

(51) Int. Cl.$^7$ ............................................ A61B 18/18
(52) U.S. Cl. .............................. 606/10; 606/3; 606/5; 606/12; 235/382; 235/487
(58) Field of Search .................... 606/3–19; 235/382, 235/487, 488, 495; 902/26

(56) References Cited

U.S. PATENT DOCUMENTS

| 4,361,775 A | * | 11/1982 | Sidline et al. ............ 235/382 |
| 4,396,914 A | * | 8/1983 | Aston ........................ 235/382 |
| 4,665,913 A | | 5/1987 | L'Esperance ............ 128/303.1 |
| 4,669,466 A | | 6/1987 | L'Esperance ............ 128/303.1 |
| 4,721,379 A | * | 1/1988 | L'Esperance .................. 606/5 |
| 4,732,148 A | | 3/1988 | L'Esperance ............ 128/303.1 |
| 4,770,172 A | | 9/1988 | L'Esperance ............ 128/303.1 |
| 4,773,414 A | | 9/1988 | L'Esperance ............ 128/303.1 |
| 5,249,121 A | | 9/1993 | Baum et al. |

FOREIGN PATENT DOCUMENTS

| DE | 2937598 | * | 3/1981 | .................. 606/10 |
| EP | 0247260 | | 12/1987 | ............ A61B/3/10 |

OTHER PUBLICATIONS

English translation of DE 2937598 (Mar. 19, 1981) by idem Translation Center, Inc., 614 Greer Road, Palo Alto, CA 94303, pp. 1–11.

* cited by examiner

Primary Examiner—David M. Shay
(74) Attorney, Agent, or Firm—Townsend and Townsend and Crew LLP

(57) ABSTRACT

An ophthalmological laser surgery system having a laser, associated elements for delivering an optical beam from the laser to a patient eye location, a control unit for controlling the operation of the system and a system input/output device, is enabled by a patient data card. The data card originally contains both patient background and system control information, which is transferred to the control unit via the input/output device. During system operation, newly generated information, such as laser beam power, is stored in the data card to provide an independent record of the surgical procedure actually performed. After one use, the data card is invalidated to prevent further use.

17 Claims, 1 Drawing Sheet

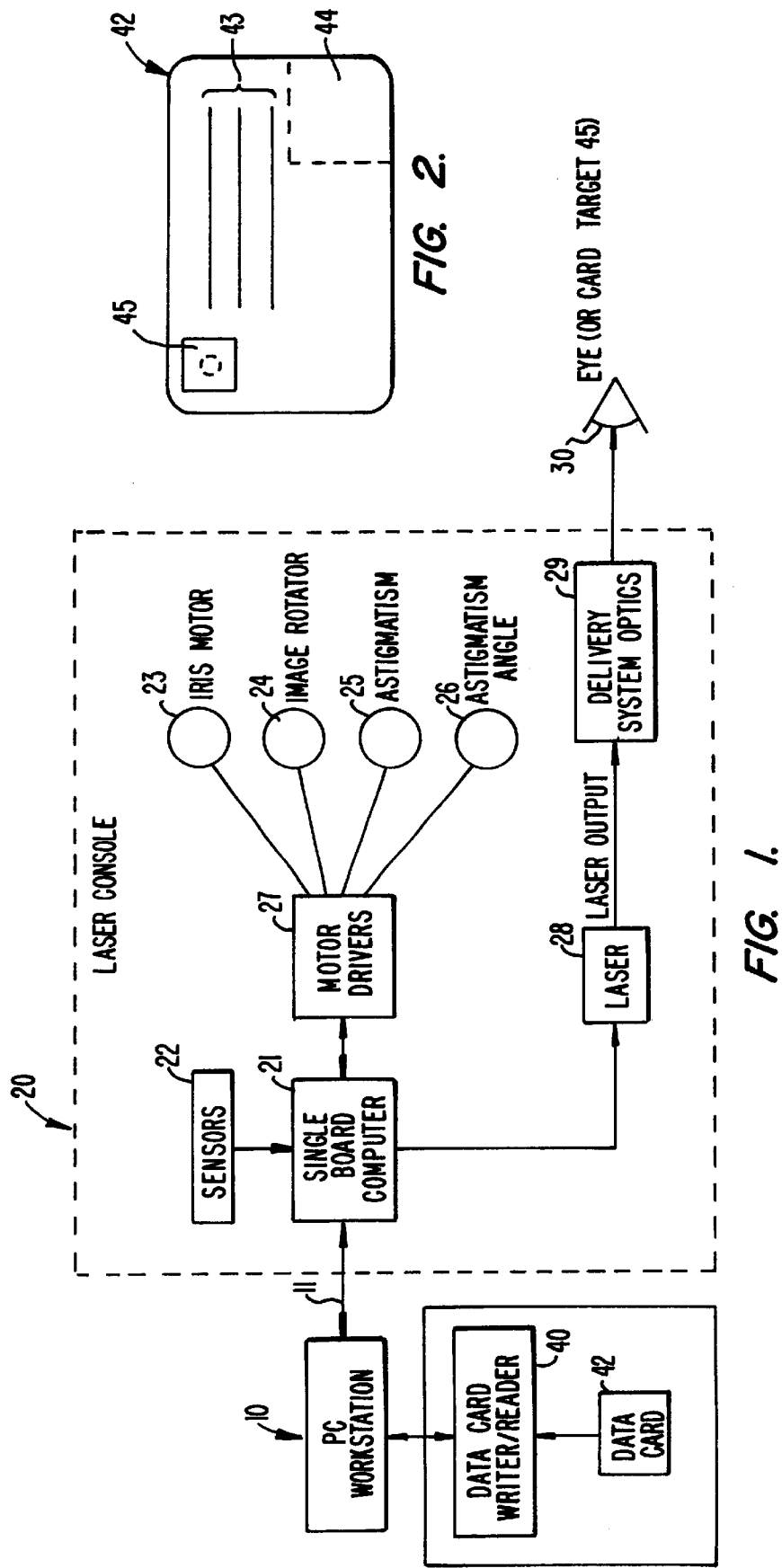

OPHTHALMOLOGICAL SURGERY TECHNIQUE WITH ACTIVE PATIENT DATA CARD

This is a continuation application of U.S. patent application Ser. No. 07/666,840, filed Mar. 8, 1991, the disclosure of which is herein incorporated by reference.

BACKGROUND OF THE INVENTION

This invention relates to ophthalmological surgery techniques which employ an ultraviolet laser used to provide ablative photodecomposition of the surface of the cornea in order to correct vision defects.

Ultraviolet laser based systems and methods are known for enabling ophthalmological surgery on the external surface of the cornea in order to correct vision defects by the technique known as ablative photodecomposition of the cornea. In such systems and methods, the irradiated flux density and exposure time of the cornea to the ultraviolet laser radiation are so controlled as to provide a surface sculpting of the cornea to achieve a desired ultimate surface change in the cornea, all in order to correct an optical defect. Such systems and methods are disclosed in the following U.S. patents and patent applications, the disclosures of which are hereby incorporated by reference: U.S. Pat. No. 4,665,913 issued May 19, 1987 for "Method for Ophthalmological Surgery"; U.S. Pat. No. 4,669,466 issued Jun. 2, 1987 for "Method and Apparatus for Analysis and Correction of Abnormal Refractive Errors of the Eye"; U.S. Pat. No. 4,732,148, issued Mar. 22, 1988 for "Method for Performing Ophthalmic Laser Surgery"; U.S. Pat. No. 4,770,172 issued Sep. 13, 1988 for "Method of Laser-Sculpture of the Optically Used Portion of the Cornea"; U.S. Pat. No. 4,773,414 issued Sep. 27, 1988 for "Method of Laser-Sculpture of the Optically Used Portion of the Cornea; U.S. patent application Ser. No. 109,812 filed Oct. 16, 1987 for "Laser Surgery Method and Apparatus"; and U.S. patent application Ser. No. 081,986 filed Aug. 5, 1987 for "Photorefractive Keratectomy".

The art has now advanced to the stage at which self-contained laser based systems are sold as stand alone units to be installed in a surgeon's operatory or a hospital, as desired. Thus, hospitalization is not necessarily required in order to perform such ophthalmological surgery. Such systems typically include a p.c. (personal computer) type work station, having the usual elements (i.e., keyboard, video display terminal and microprocessor based computer with floppy and hard disk drives and internal memory), and a dedicated microprocessor based computer which interfaces with the p.c. work station and appropriate optical power sensors, motor drivers and control elements of the ultraviolet laser, whose output is delivered through an optical system to the eye of the patient. In use, after the patient has been accommodated on a surgery table or chair, the system is controlled by the operator (either the surgeon or the surgeon and an assistant) in order to prepare the system for the delivery of the radiation to the patient's eye at the appropriate power level and spatial location on the corneal surface. Patient data is typically entered, either manually via the p.c. work station keyboard or from a memory storage element (e.g., a floppy disk), and the system automatically calculates the beam delivery parameters and displays the resulting calculations on the video display terminal, with an optional hard-copy printout via a suitable printer. The laser is also prepared to deliver the appropriate radiation in accordance with the calculated beam delivery parameters, and the delivery system optics are likewise preconditioned. In some systems, a provision is made for permanently recording on a plastic card made of PMMA (polymethylmethacrylate) a spot image of the laser beam used in the surgical operation. This spot is recorded prior to the operation to ensure that the beam power is properly adjusted and to provide a permanent record of the beam used. PMMA is typically used due to the characteristic of this material of having a closely similar ablative photodecomposition response to that of the human corneal tissue. After the surgery has been performed, the resultant data is typically made part of a permanent record, which becomes part of the patient's file.

Such systems and methods are presently emerging as the technique of choice for ophthalmological surgery to correct various vision defects in humans. However, as a relatively recent development this technique in general is still subject to close scrutiny and careful evaluation by the medical community as well as by certain regulatory agencies (e.g., the Food and Drug Administration in the United States of America). Although the p.c. work station provides some ability to collect pertinent information for the evaluation of system performance and to aid in tracking the efficacy of the surgical technique, as well as to provide quality control assistance to the manufacturer of the system, existing laser systems lack a simple effective control mechanism for this purpose.

SUMMARY OF THE INVENTION

The invention provides a simpe control mechanism for monitoring the actual usage of ophthalmological laser surgery systems, which is relatively inexpensive to implement and highly reliable in tracking information relating to machine usage and patients' data relating to surgeries performed.

In a first aspect of the invention, an ophthalmological laser surgery system is provided with a patient data card read/write device for controlling and monitoring the operation of the laser surgical system in conjunction with a pre-coded patient data card. The data card and read/write device interact in such a manner that the laser surgical system cannot be operated unless an authorized patient data card is inserted into the read/write device. Once the patient data card is recognized by the system as a legitimate and authorized card, the system is unlocked for normal operation. Preferably, during normal operation the beam delivery parameters calculated by the system, as well as other actual surgical operation data (such as the configuration of the delivery system optics, the duration and power of the laser irradiation of the patient's cornea, the coordinates of the projected laser beam, and the like) are recorded on the patient data card to form a permanent record independently of or parallel to the information stored in the p.c. work station. Also, a test spot of the actual laser beam can be permanently recorded onto the patient data card by directing the beam onto a preselected region of the data card to perform an ablation of that region.

In another aspect, the invention comprises a patient data card having encoded therein several kinds of information for use in evaluating and controlling a laser based ophthalmological surgery system and surgeries performed therewith. A first type of information comprises an authorization code required by the surgery system for enablement to an operative state. Preferably, this first type of information includes a code unique to a specific laser surgery system so that a given patient data card can be used on one and only one machine. Further information stored on the card identifies all authorized surgeons, the patient, the patient's past history, the desired prescription or other identifying information regarding the permissible surgery to be performed on that patient, and preoperative diagnostic information for checking the laser system settings. The card may also contain downloadable software for controlling or altering the operation of the laser system. The card may also contain a photograph of the patient, one or more fingerprints of the patient, or a combination of this or other identifier information. In addition, the card preferably contains an ablation region capable of forming and retaining a physical laser ablation imprint of the intended laser treatment for future analysis and comparison.

In use, the card is pre-coded by the system manufacturer or some other control agency, and issued for use with a specific system. If desired, the patient information may be intentionally left blank and provided by the surgeon or some other authorized person prior to the surgical operation. After the surgery has been performed, the actual data pertaining to the surgery is encoded onto the card for future use. Preferably, the data card is issued for a single surgery and is invalidated immediately thereafter, e.g., by permanently recording an invalidation character onto the card.

The data stored on the card can be transferred from the card to any one of a number of interested parties. The surgeon, for example, may transfer the information from the card to a patient data file or some other master file maintained by the surgeon. This can be done at the data card read/write device and the p.c. work station at the site of the laser system. In addition, the information recorded in the patient data card can be transferred to the system manufacturer's files either from the surgeon's office using the p.c. work station and a modem, or directly from the patient data card. In the latter case, the card can be physically transferred to the manufacturer's office by either the surgeon or the patient, or the patient may visit one of a number of convenient sites having a compatible card reader device.

For a fuller understanding of the nature and advantages of the invention, reference should be had to the ensuing detailed description taken in conjunction with the accompanying drawings.

BRIEF DESCRIPTION OF THE DRAWINGS

FIG. 1 is a block diagram of an ophthalmological laser surgery system incorporating the invention; and FIG. 2 is a plan view of a patient data card according to the invention.

DESCRIPTION OF THE PREFERRED EMBODIMENTS

Turning now to the drawings, FIG. 1 illustrates a block diagram of an ophthalmological surgery system incorporating the invention. As seen in this Fig., a p.c. work station 10 is coupled to the single board computer 21 of a laser surgery unit 20 by means of a first bus connection 11. P.C. work station 10 and the subcomponents of laser surgery unit 20 are known components and preferably comprise the elements of the VISX TWENTY/TWENTY excimer laser system available from Visx, Incorporated of Sunnyvale, Calif. Thus, the laser surgery system 20 includes a plurality of sensors generally designated with reference numeral 22 which produce feedback signals from the moveable mechanical and optical components in the laser optical system, such as the elements driven by an iris motor 23, an image rotator 24, an astigmatism motor 25 and an astigmatism angle motor 26. The feedback signals from sensors 22 are provided via appropriate signal conductors to the single board computer 21, which is preferably an STD bus compatible single board computer using a type 8031 microprocessor. The single board computer 21 controls the operation of the motor drivers generally designated with reference numeral 27 for operating the elements 23–26. In addition, single board computer 21 controls the operation of the excimer laser 28, which is preferably an argon-fluorine laser with a 193 nanometer wavelength output designed to provide feedback stabilized fluence of 160 mJoules per $cm^2$ at the cornea of the patient's eye 30 via the delivery system optics generally designated with reference numeral 29. Other ancillary components of the laser surgery system 20 which are not necessary to an understanding of the invention, such as a high resolution microscope, a video monitor for the microscope, a patient eye retention system, and ablation effluent evacuator/filter, and the gas delivery system, have been omitted to avoid prolixity. Similarly, the keyboard, display, and conventional p.c. subsystem components (e.g., flexible and hard disk drives, memory boards and the like) have been omitted from the depiction of the p.c. work station 10.

P.C. work station 10 is actively intercoupled with a patient data card writer/reader 40 designed to interact with an individual patient data card 42 schematically illustrated in FIG. 2. As seen in FIG. 2, the patient data card 42 is similar to a credit card and has a first surface region 43 for carrying visually readable information, such as the name of the patient, the card supplier (e.g., laser surgery system manufacturer, health care provider or the like), the patient's name and any other information which is deemed desirable for visual presentation. Another region 44 is reserved for information identifying the authorized bearer or user of the card, such as a fingerprint or a photograph of the patient. An ablation region or target area 45 is provided for permanently recording the laser beam operating characteristics just prior to or after performance of a surgery. For this purpose, ablation region 45 may comprise an insert of a polymethylmethacrylate, which as noted above has close matching ablative photodecomposition characteristics to that of human corneal tissue. Alternatively, the entire card 42 may be fabricated of PMMA, or some other substance such as polycarbonate which has similar ablation characteristics to PMMA. The purpose of the ablation region 45 is to provide a permanent ablative photodecomposition record produced by the actual laser beam used in the surgery.

Patient data card 42 is preferably an optical memory card of the type manufactured and marketed by Drexler Technology Corporation under the trademark LaserCard, which is a credit card sized optical data storage device capable of holding more than four megabytes of write once/read many (WORM) data. Similarly, the data card writer/reader 40 may be a known unit compatible with the Drexler optical memory card. If desired, a suitable magnetic memory card may be employed along with a compatible card writer/reader device 40.

The patient data card 42 is initially provided with read only information optically encoded into the subsurface recording layers (not visible in FIG. 2). This information includes the serial number or other identifying characteristic of a specific laser surgery system 20 so that the data card 42 can only be used with a specific system 20. The purpose for this limitation is to provide controlled information relating to the amount of use of the system 20 and a match between the identity of the system 20 and the actual beam used during the eye surgery (the ablation record permanently formed in ablation region 45 of the data card 42). In addition, other qualifying data may be permanently recorded by the card producer, such as the personal identification number of the surgeon or surgeons (or other personnel) qualified to operate the specific system 20, the prescription of the patient to control the amount and type of laser surgery on a particular patient, the eye upon which surgery will be allowed (e.g., right eye only, left eye only or both, including any differences in prescription between the two eyes), and any other relevant and pertinent information deemed desirable for monitoring the specific patient and the specific system 20.

In order to render the system 20 operative, an authorized data card 42 must be read by the writer/reader 40, and this information must then be presented to the p.c. work station 10, which functions as the master control for the system 20. Once an authorized card has been inserted and identified, the operation of the system 20 proceeds in a somewhat conventional fashion in that the beam delivery parameters are calculated in the p.c. work station 10 and transferred to the single board computer 21 for control of the various motors 23–26, the laser 28 and the delivery system optics 29. At some time during the surgery procedure, preferably just prior to the actual irradiation of the eye 30, the data card 42 may be installed in a fixture (not shown) in the output beam path of the laser 28 (i.e., within the delivery system optics 29 or at the output side thereof and the laser 28 is pulsed at the surgical rate and power to form the permanent record of the laser beam in the ablation region 45. Thereafter, the surgery is performed and the post operation data is measured, calculated and stored in an appropriate memory location within the p.c. work station 10. Certain information may then be recorded onto the patient data card 42 by means of the data card writer/reader 40 so that the data card 42 obtains post operative information useful for monitoring purposes. For example, the date of the operation, the total length of the exposure of the corneal surface of the eye 30 to the laser beam 28, the pulse duration, the time between pulses, the exact coordinate settings of the laser beam radiation throughout the operation may all be recorded on the patient data card 42. This information is then available until destruction of the card for any informational purposes the surgeon, the patient, the health insurance company, the regulatory agency and the system manufacturer may require. In addition, if desired the card 42 may be permanently altered to prevent repeated use with specific surgery system 20 or any other system 20 as an added check on the operational use of a specific system 20.

The patient data card 42 may contain program instructions required for the operation of the system 20. In such an embodiment, p.c. workstation 10 receives the necessary program instructions from the card 42 using a conventional software downloading operation at the beginning of system operation. At the conclusion of system operation, the program instructions resident in the p.c. workstation 10 are erased to prevent subsequent operation of system 20 without a fresh data card 42.

As will now be apparent, laser surgery systems provided with the personal data card functioning as a control token offer an unparalleled degree of control over the use of the surgery system and afford a rigorous information gathering capability for quality control and monitoring studies. In particular, every single use of a given surgery system 20 can be accurately monitored by use of the patient data card 42, and the actual operating characteristics and optical parameters can be permanently stored in an independently verifiable manner for future study. Such a capability is particularly important for laser surgery systems still subject to regulatory control, as well as to fully approved laser surgery systems for which cumulative historical data is highly desirable. The added cost of the data card reader/writer 40 is nominal compared to the overall system, and the patient data card is no more inconvenient to carry and use than any conventional credit card.

While the above provides a full and complete disclosure of the preferred embodiments of the invention, various modifications, alternate constructions and equivalents may be employed as desired. For example, while the invention has been described with specific reference to an optically encoded data card 42, data cards having read/write storage capability and using magnetic or semiconductor technology may be employed, as desired. In addition, other laser surgery systems than the VISX system noted above can be used to implement the invention. Therefore, the above description and illustrations should not be construed as limiting the invention, which is defined by the appended claims.

What is claimed is:

1. For use with a ophalmological laser surgery system that ablates the cornea by controlled irradiation, the laser surgery system having a system control unit which is enabled to perform a corneal ablation procedure in response to predetermined enabling information, a device comprising:

a data card bearing said predetermined enabling information, the data card being permanently altered by the system in response to the corneal ablation procedure so as to inhibit the data card from enabling the system.

2. The invention of claim 1, wherein the data card is further configured to store at least one surgical parameter actually employed during a surgical procedure by the laser surgery system.

3. The invention of claim 1, wherein the data card is further configured to store program instructions to operate the laser surgery system.

4. The invention of claim 1, wherein the predetermined enabling information comprises an information relating to a surgeon authorized to operate the system.

5. An opthalmological laser surgery system that ablates the cornea by controlled irradiation, said system comprising:

a data card containing predetermined enabling information including a predetermined type of laser surgery, wherein said data card is issued from a manufacturer of the laser surgery system and is pre-coded by the manufacturer with at least a portion of the enabling information including the predetermined type of laser surgery; and a system control unit configured to permit a corneal ablation procedure in response to the predetermined enabling information, wherein said system control unit is impeded from performing a corneal ablation procedure of a type of laser surgery that is different than said predetermined type, and a laser emitting a cornea ablating beam, coupled to the control unit and controlled thereby.

6. The invention of claim 5 wherein said predetermined type of laser surgery comprises myopic photorefractive keratectomy.

7. The invention of clam 5 wherein said predetermined type of laser surgery comprises hyperopic photorefractive keratectomy.

8. The invention of claim 5 wherein said predetermined type of laser surgery comprises astigmatic photorefractive keratectomy.

9. The invention of claim 5 wherein said predetermined enabling information further includes a predetermined amount of laser surgery; and wherein the system control unit is impeded from performing a corneal ablation procedure of an amount of laser surgery that is greater than said predetermined amount.

10. An opthalmological laser surgery system that ablates the cornea by controlled irradiation, said system comprising:
   a data card bearing predetermined enabling information; and
   a system control unit means for
      (a) reading the predetermined enabling information on the data card,
      (b) enabling a corneal ablation procedure in response to the predetermined enabling information, and
      (c) permanently altering the data card after the corneal ablation procedure has been performed so that the data card is thereafter incapable of enabling the system.

11. The invention of claim 10 wherein the system control unit further requires program instructions to operate the laser surgery system, and includes means for
   (a) reading required program instructions to operate the laser surgery system from said data card, and
   (b) performing said corneal ablation procedure in response to at least some of said program instructions supplied by the patient data card.

12. The invention of claim 10 further comprising a card reader that, when presented with the data card, reads the predetermined information from the data card into the system control unit.

13. The invention of claim 10 wherein the system control unit further includes means for comparing an information carried by the data card relating to an authorized surgeon with a unique identifier in the system control unit.

14. The invention of claim 10 wherein said system control unit further includes means for recording on the data card at least one surgical parameter actually employed during the corneal ablation procedure by the laser surgery system.

15. The invention of claim 14 wherein said surgical parameter comprises a characteristic of the laser beam actually employed during a surgical procedure.

16. An opthalmological laser surgery system that ablates the cornea by controlled irradiation, said system comprising:
   a data card bearing predetermined enabling information; and
   a system control unit including means for
      (a) reading the predetermined enabling information on the data card,
      (b) enabling a corneal ablation procedure in response to the predetermined enabling information, and
      (c) permanently altering the data card after the corneal ablation procedure has been performed so that the data card is thereafter incapable of enabling the system so as to effect regulatory control of laser ablation procedures performed by the laser surgery system per a regulatory agency.

17. An opthalmological laser surgery system that ablates the cornea by controlled irradiation, the use of which is prevented by unauthorized personnel, said system comprising:
   an independent data carrier containing predetermined information including the identity of a surgeon authorized to operate said specific system; and
   a system control unit including means for
      (a) storing a unique identifier, said unique identifier specifying the identity of a surgeon authorized to operate said specific system
      (b) comparing the unique identifier in the system control unit with the identity of the authorized surgeon specified by the predetermined information contained in the independent data carrier,
      (c) enabling a corneal ablation procedure if the unique identifier matches the identity of the surgeon, and
      (d) permanently altering the data card after the corneal ablation procedure has been performed so that the data card is thereafter incapable of enabling the system.

\* \* \* \* \*